United States Patent [19]

Dickman et al.

[11] Patent Number: 5,169,961

[45] Date of Patent: Dec. 8, 1992

[54] PROCESS FOR THE PRODUCTION OF 2-ACETYLBENZO [β] THIOPHENES

[75] Inventors: Daniel A. Dickman, Grayslake; Bruce W. Horrom, Waukegan; Brian A. Roden, Mundelein; Sanjay R. Chemburkar, Gurnee, all of Ill.

[73] Assignee: Abbott Laboratories, Abbott Park, Ill.

[21] Appl. No.: 796,298

[22] Filed: Nov. 22, 1991

[51] Int. Cl.$^5$ .............................. C07D 333/56
[52] U.S. Cl. ............................................. 549/57
[58] Field of Search ................................. 549/52

[56]       References Cited
           U.S. PATENT DOCUMENTS

| | | | |
|---|---|---|---|
| 2,634,200 | 4/1953 | Schlesinger | 71/90 |
| 2,634,201 | 4/1953 | Moury et al. | 71/90 |
| 2,634,202 | 4/1953 | Fincke | 568/28 |
| 2,673,856 | 3/1954 | Emerson | 549/57 |
| 4,873,259 | 10/1989 | Summers, Jr. et al. | 549/55 |

OTHER PUBLICATIONS

D. Leaver, et al, *J. Chem. Soc*, "Heterocyclic Iso-η-electronic Analogues of Azalene," pp. 740–748 (1962).

F. Mayers, *Ann*, "Farbstoffstadien in Thionaphtenreihe," 488, 259–296 (1931).

"M. Farrar, *J. Am. Chem Soc*, Condensation Effected by Acidic Catalysts," 72, pp. 4433–4436 (1950).

O. M. Corrigan et al., *Aust. J. Chem.*, "Cobalt Complexes of Bi-and Tetro-dentate N-substituted O-Mercaptobengaldimines," 29, pp. 1413–1427 (1976).

H. Kasmai, et al, *Synthesis*, "An Efficient and convenient Synthesis of 2-Mercaptobenzaldehyde," Oct. 1989, pp. 763–765.

*Primary Examiner*—Richard L. Raymond
*Assistant Examiner*—Mark W. Russell
*Attorney, Agent, or Firm*—Jerry F. Janssen

[57]               ABSTRACT

A process for the production in high yield of 2-aceylbenzo[β]thiophene and its alkyl and alkoxy substituted derivatives by converting a 2-halobenzaldehyde to a 2,2'-dithiobis(benzaldehyde) intermediate and reacting that intermediate successively with 2,4-pentanedione and chloroacetone in the presence of base.

14 Claims, No Drawings

PROCESS FOR THE PRODUCTION OF 2-ACETYLBENZO [β] THIOPHENES

TECHNICAL FIELD

The present invention relates to chemical processes. More particularly, the present invention concerns a process for the production of 2-acetylbenzo[β]thiophenes and to novel intermediates in that process.

BACKGROUND OF THE INVENTION

2-Acetylbenzo[β]thiophene and its substituted derivatives are useful intermediates in the production of valuable chemical end-products which include lubricant additives, rubber vulcanization accelerators, herbicides, dystuffs and pharmaceutical agents. For example, U.S. Pat. No. 4,873,259 discloses the use of substituted 2-acetylbenzo[β]thiophenes as intermediates in the production of a class of N-hydroxyurea and acetohydroxamic acid compounds which have pharmacological activity as lipoxygenase inhibitors.

2-Acetylbenzo[β]thiophene itself is a known compound, its synthesis in low yield reported by F. Mayer, et al., Ann., 488: 259-296 (1931) by the reaction between the sodium salt of 2-sulfhydrylbenzaldehyde and chloroacetone. A similar method of preparing 2-acylbenzo[β]thiophenes by condensation of chloromethyl ketones with 2-sulfhydrylbenzaldehyde has been reported by M. Martynoff, et al., Bull. Soc. Chim., Section 5: 736–738 (1952). The preparation of 3-chloro-2-acetylbenzo[b]thiophene by chlorination of 2-acetylbenzo[b]thiophene is disclosed in U.S. Pat. No. 2,673,856. U.S. Pat. Nos. 2,634,200; 2,634,201; and 2,634,202 disclose herbicidal compositions containing 2-acylbenzo[b]thiophenes prepared by the Lewis acid catalyzed reaction between benzo[b]thiophene and acyl chlorides. M. W. Farrar, et al., J. Am. Chem. Soc.,: 4433-4436 (1950) report the preparation of 2-acetylbenzo[β]thiophene by the acetylation of benzo[β]thiophene with acetic anhydride in the presence of a Lewis acid catalyst.

The methods for preparing 2-acetylbenzo[b]thiophene and its substituted derivatives which have been disclosed in the literature suffer from one or more of several shortcomings when evaluated as a commercially viable method of preparing 2-acetylbenzo[β]thiophene. In some cases prior art processes involve acylation of benzo[β]thiophene, a comparatively expensive starting material; in other cases, the starting material is 2-sulfhydrylbenzaldehyde, a comparatively unstable intermediate, difficult to synthesize. For example, D. Leaver, et al., J. Chem. Soc., 1962, 740, report the synthesis of reports the synthesis of 2-mercaptobenzaldehyde in 38% overall yield from 2,2'-dithiobis(benzoic acid) and M. F. Corrigan, et al., Aust. J. Chem., 29: 1413, (1976) report its synthesis in 14–17% overall yield from 2-nitrobenzaldehyde. H. Kasmai, et al., Synthesis, October 1989, pp. 763–765, report the synthesis of 2-mercaptobenzaldehyde in 52% overall yield from 2-mercaptobenzoic acid.

There is thus a need for a process for the preparation of 2-acetylbenzo[b]thiophene and its derivatives which makes use of inexpensive, readily available, and chemically stable starting materials and intermediates and which produces the desired end-product in high overall yield and purity.

DETAILED DESCRIPTION OF THE INVENTION

The present invention provides a facile and commercially attractive process for the preparation of derivatives of 2-acetylbenzo[β]thiophenes of the formula

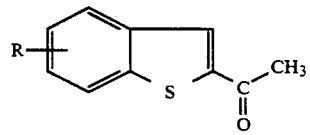

where R is selected from hydrogen, alkyl of from one to six carbon atoms, and alkoxy of from one to six carbon atoms, employing the steps outlined in the General Reaction Scheme shown below.

In the first step of the reaction a 2-substituted benzaldehyde, I, is reacted with a sterically encumbered mercaptan, $R^2SH$, in a polar organic solvent in the presence of base. The starting material is selected from a 2-halobenzaldehyde, with R-substituted (where R is alkyl or alkoxy) or unsubstituted 2-chlorobenzaldehyde being the preferred reactants.

By "sterically encumbered" mercaptan is meant a mercaptan in which the carbon atom bearing the sulfhydryl group is preferably a secondary or tertiary carbon atom with tertiary mercaptans being particularly preferred. Suitable mercaptans for this step of the process include, for example, secondary and tertiary mercaptans of between three and twelve carbon atoms such as 2-propanethiol, 2-butanethiol, 2- or 3-pentanethiol, 1,1-dimethylethanethiol, 1,1-dimethylpropanethiol, 1,1-diethylethanediol, 1,1-diethylpropanethiol, and the like. The preferred mercaptan for this step of the process is 1,1-dimethylethanethiol (tert-butyl mercaptan).

Suitable solvents for carrying out this step of the process include dimethylsulfoxide, N,N-dimethylformamide, tetrahydrofuran, dimethoxyethylene (DME), General Reaction Scheme

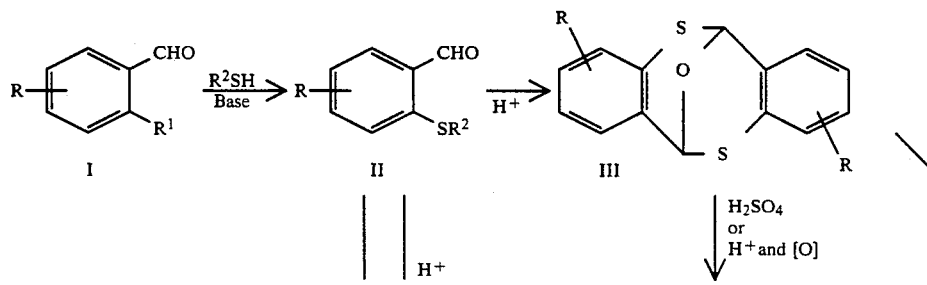

General Reaction Scheme

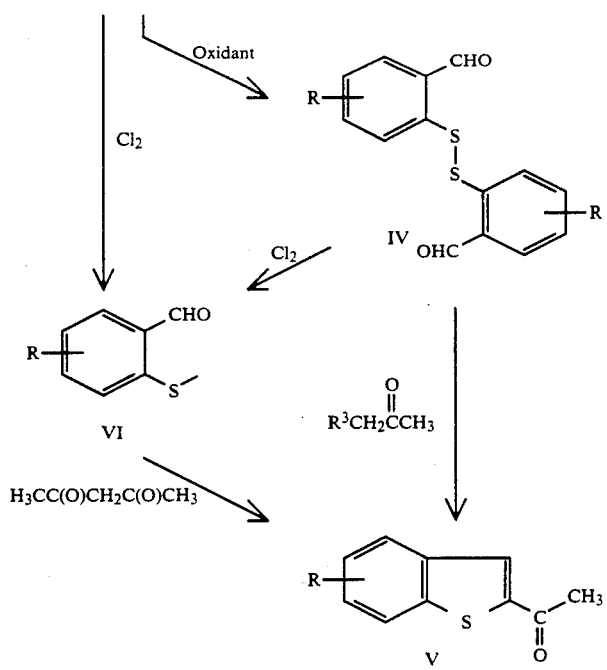
-continued acetonitrile, and alcohols of from one to four carbons. The preferred solvent is dimethylsulfoxide. The base is selected from sodium or potassium carbonate, sodium or potassium hydroxide, potassium phosphate, dipotassium hydrogen phosphate, sodium hydride, or sodium or potassium alkoxides of alcohols of from one to four carbon atoms. When the reaction is carried out in an alcohol, the base can be generated in situ, by first adding a metal such as potassium or sodium to the solvent. In dimethylsulfoxide, the preferred base is potassium hydroxide.

This step of the reaction is typically carried out at a temperature of between ambient and the boiling point of the solvent (under reflux) for a period sufficient to bring about essentially complete conversion of the starting material to the 2-alkylthiobenzaldehyde, II, with temperatures between about 50° C. and 80° C. being preferred. The course of the reaction can be conveniently followed by thin-layer chromatographic analysis of the reaction mixture. Depending upon the choice of starting material, mercaptan, and base, the reaction time can range between about 1–3 hours up to about 100 hours for completion. When the starting materials are the preferred 2-chlorobenzaldehyde and tert-butyl mercaptan and the reaction is carried out in dimethylsulfoxide in the presence of potassium hydroxide, the reaction times are short, ranging typically between about 1–3 hours.

In the preferred second step of the process of this invention, the 2-alkylthiobenzaldehyde, II, is converted by oxidation in the presence of an acid to 2,2'-dithiobis(-benzaldehyde), IV. The acid employed in this step of the reaction is preferably acetic acid, but may be any low molecular weight water-soluble organic acid of from two to four carbon atoms mixed with a strong inorganic acid. The reaction is preferably carried out in the presence of water. The oxidizing agent is selected from bromine; chlorine; cupric salts such as the acetate or chloride; hypohalic acids such as HOCl and HOBr; N-bromo- and N-chlorosuccinimide, and alkali metal bromates or iodates. The preferred oxidant for this step of the process is bromine.

The reaction can be carried out in an organic acid, preferably acetic acid, as the sole solvent with a stoichiometric equivalent of the oxidant added (preferably bromine) or, alternatively, in a mixture of an organic acid and a polar co-solvent such as dimethylsulfoxide, N,N-dimethylformamide, 2,5-dioxapentane (dimethoxyethylene, DME), or acetonitrile. In one preferred method of carrying out this step of the process, the solvent is a mixture of acetic acid and dimethylsulfoxide with aqueous hydrohalic acid (hydrochloric or hydrpbromic acid), most preferably hydrobromic acid ranging in initial concentration between about 15% and 48% by weight, present in an amount of from one to three equivalents, based on the amount of the starting substituted benzaldehyde. While not holding to one theory to the exclusion of others, it is believed that under these conditions a reduction-oxidation reaction between the hydrogen bromide and dimethylsulfoxide results in the production of dimethyl sulfide and bromine with the latter material serving as the oxidant to produce 2,2'-dithiobis(benzaldehyde), IV. In an alternative preferred method of carrying out this step of the process which avoids the production of dimethylsulfude, the 2-alkylthiobenzaldehyde, II, is reacted in the presence of bromine and an organic solvent, preferably acetic acid, with the reduction product, HBr, aiding in the reaction.

In an alternative route to the intermediate, 2,2'-dithiobis(benzaldehyde) IV, the 2-alkylthio-benzaldehyde, II, may be reacted with hydrobromic acid in water or an organic acid such as acetic acid to produce the stable intermediate, 2,6-dithio-9-oxadibenzo[c,g]bicyclo-[3.3.1]nonane, III. This material can be subsequently converted by the action of sulfuric acid or other oxidizing agent in acidic medium to 2,2'-dithiobis(benzaldehyde), IV, or alternatively, by allowing IV to react further with 2,4-pentanedione in the presence of sulfuric acid to the end-product 2-acetylbenzo[β]thiophene, V. In the latter reaction, it is believed that III is converted, first to 2,2-dithiobis(benzaldehyde), IV, which is then converted to the product by reaction with 2,4-pentanedione with 2-thiobenzaldehyde as a by-product. The sulfuric acid then believed to oxidize two equivalents of the thiol to 2,2'-dithiobis(benzaldehyde) in a cyclical process. The reaction can thus be carried out in the presence of acid and another oxidant such as sodium periodate, etc.

In the third step of the process of this invention, 2,2'-dithiobis(benzaldehyde), IV, is reacted with a derivative of acetone, $R^3CH_2C(O)CH_3$, to produce the final product, 2-acetylbenzo[β]thiophene, V. In the preferred method of carrying out this step of the process, the 2,2'-dithiobis(benzaldehyde), IV, is reacted sequentially first with one equivalent of 2,4-pentanedione (acetylacetone) in a polar solvent such as methanol in the presence of base. The base is selected from sodium and potassium carbonate, and sodium and potassium hydroxide, with potassium carbonate being preferred. The reaction is carried out at temperatures ranging between about ambient and 60° C. for a period sufficient to go to completion to produce about one equivalent of 2-acetylbenzo[β]thiophene and about one equivalent of the anion, VII:

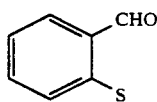
VII

Subsequently, at the end of this period, one equivalent of chloro-or bromoacetone, preferably chloroacetone, is added to the reaction mixture to produce an additional equivalent of 2-acetylbenzo[β]thiophene. This can also be carried out with two equivalents of 2,4-pentanedione in a polar solvent such as methanol in the presence of a base such as potassium carbonate. The reaction is carried out at a temperature ranging between about 0° C. and 60° C. in the presence of an oxidizing agent such as potassium periodate or catalytic amounts of copper in the presence of atmosphereic oxygen. It is believed that the reaction proceeds by reaction of IV with 2,4-pentanedione to give 2-acetylbenzo[β]thiophene and the anion of 2-thiobenzaldehyde. The oxidizing agent is believed to convert two equivalents of the anion to IV in a cyclical process.

In another alternative embodiment of the process of the present invention, the 2-alkylthiobenzaldehyde, II, is converted by the action of chlorine in an unreactive solvent such as dichloromethane to 2-chlorothiobenzaldehyde, VI. This intermediate, which can be used without isolation in the next step, is reacted with 2,4-pentanedione in the presence of a base such as potassium or sodium carbonate (preferably potassium carbonate) to produce the substituted or unsubstituted 2-acetylbenzo[β]thiophene, V. The intermediate VI can also be formed by reaction of IV with one equivalent of chlorine.

EXAMPLE 1

Preparation of 2-(1,1-Dimethylethylthio)benzaldehyde from 2-Chlorobenzaldehyde

Powdered potassium hydroxide (21.9 g, 390 mmol) and 56 ml (497 mmol) of terbutyl mercaptan were mixed 55.5 ml of dimethylsulfoxide in a 250 ml three-neck flask. To this stirred mixture was added dropwise over a ten minute period 50 g (356 mmol) of 2-chloro-benzaldehyde. During addition of the 2-chlorobenzaldehyde, the reaction mixture warmed to 120° C. After addition was complete, the mixture was allowed to react at about 110° C. for 1.5 hours. At the end of this time, the mixture was cooled to room temperature and taken up on 600 ml of ethyl acetate and 1 liter of water. The organic layer was separated, dried and evaporated to yield 2-(1,1-dimethylethylthio)benzaldehyde, b.p. 80°-82° C. at 0.05 mm Hg, which was used without further purification in the next step of the process.

EXAMPLE 2

Preparation of 2,2'-Dithiobis(benzaldehyde by Reaction of 2-(1,1-Dimethylethylthio)benzaldehyde with Hydrogen Bromide in Dimethylsulfoxide 2,2'-Dithiobis(benzaldehyde) (7.0 g, 36 mmol), was mixed in a 100 ml roundbottom flask with 2.68 g (36 mmol) of potassium chloride, 5.3 ml of dimethylformamide, and 4.97 g (36 mmol) of potassium carbonate. To this mixture was slowly added ($CO_2$ evolution) a solution of 63 ml of 15% hydrogen bromide in acetic acid containing 1.92 ml of dimethylsulfoxide (1.92 ml) and a small amount of water (0.32 ml).

When addition was complete, the reaction was allowed to proceed at room temperature, with the course of the reaction being followed by thin-layer chromatography, eluting with 30% ethyl acetate in hexanes. The reaction was essentially complete after two hours, at which time the reaction mixture was successively washed with 300 ml of 20% sodium hydroxide, and twice with 75 ml portions of dichloromethane. The organic layers were separated, dried over anhydrous magnesium sulfate and concentrated under vacuum to yield 4.35 g (31.3 mmol, 87%) of 2,2'-dithiobis(benzaldehyde) mp 145° C., 95% pure.

EXAMPLE 3

Preparation of 2-Acetylbenzo[β]thiophene by Reaction of 2,2'-Dithiobis(benzaldehyde) Stepwise with 2,4-Pentanedione and Chloroacetone 2,2'-Dithiobis(benzaldehyde) (39.8 g, 291 mmol) was added in one lot to a stirred mixture of 14.5 g (145 mmol) of 2,4-pentanedione and 40.1 g (291 mmol) of potassium carbonate in 60 ml of dimethylsulfoxide. (Methanol can also be used as the solvent in this reaction.) The resulting mixture was allowed to react without any external cooling for a period of about forty minutes. At the end of this time, 13.4 g (145 mmol) of chloroacetone was added to the reaction mixture in one lot. The reaction mixture warmed to about 40°-50° C. and was allowed to react without any external cooling for an additional two hours.

At the end of this time, the reaction mixture was poured into 1.5 liters of ice water. The precipitated solid was collected and dried under vacuum at 48° C. for 18 hours to yield 48.0 g (547 mmol, 94%) of 2-acetylbenzo[b]thiophene, mp 87°-88° C., 98% pure.

EXAMPLE 4

Preparation of 2-Acetylbenzo[β]thiophene via 2-Chlorothiobenzaldehyde as an Intermediate To a 100 ml round-bottom flask containing 25 ml of dichloromethane, cooled to 0° C., was added 2.04 g of chlorine. 2-(1,1-Dimethylethylthio)benzaldehyde (1.86 g) was added in a dropwise manner to the stirred flask contents. After addition was complete, the mixture was stirred at 0° C. for one hour, after which the solution was purged with nitrogen gas to remove any remaining chlorine gas and the product hydrogen chloride gas. At this point, the flask contents contained 2-chlorothiobenzaldehyde which was not isolated, but employed directly in the next step.

Potassium carbonate (1.8 g) was added to the flask contents with stirring, followed by 1.02 ml of 2,4-pentanedione. The resulting mixture was allowed to warm to room temperature and react overnight. At the end of this time, 50 ml of dichloromethane was added to the flask contents which were washed with water. The organic layer was separated, dried over anhydrous magnesium sulfate, and concentrated to yield 1.36 g (7.7 mmol, 65%) of 2-acetylbenzo[b]thiophene.

EXAMPLE 5

Preparation of 2-Acetylbenzo[β]thiophene by Oxidation of 2,2'-Dithiobis(benzaldehyde) with Periodate 2,2'-Dithiobis(benzaldehyde) (1.75 g, 6.38 mmol) was dissolved in 24 ml of methanol in a 100 ml round-bottom flask. To this mixture was added 1.76 g, (12.75 mmol) of potassium carbonate and 1.31 ml of 2,4-pentanedione and 1.36 g (6.38 mmol) of sodium periodate. The mixture was stirred at room temperature for 1.5 hours after which the methanol, was removed under vacuum. The residue was taken up in 110 ml of water and extracted twice with 50 ml portions of dichloromethane. The organic layers were separated, combine, and dried over anhydrous magnesium sulfate. Removal of the dichloromethane under vacuum yielded 1.70 g (76%) of very pure 2-acetylbenzo[b]thiophene.

EXAMPLE 6

Preparation of 2,6-Dithio-9-oxa-dibenzo[c,g]bicyclo-[3.3.1]nonane 2-(1,1-dimethylethylthio)benzaldehyde (5.0 g, 25.74 mmol) and 48% aqueous hydrobromic acid (60 ml) were placed in a 100 ml round-bottom flask and the mixture was heated under reflux. After about 25 minutes, a white crystalline solid was observed in the reaction mixture. The reaction mixture was neutralized with cold 40% aqueous sodium hydroxide solution and the resulting mixture extracted with dichloromethane. The organic extract was dried and concentrated to yield 2,6-Dithio-9-oxa-dibenzo[c,g]bicyclo-[3.3.1]nonane, m.p. 155°–156° C.

EXAMPLE 7

Preparation of 2-Acetylbenzo[β]thiophene by Reaction of 2,6-Dithio-9-oxa-dibenzo[c,g]bicyclo-[3.3.1]nonane with 2,4-Pentanedione 2,6-Dithio-9-oxa-dibenzo[c,g]bicyclo-[3.3.1]nonane (0.40 g, 1.55 mmol) were mixed with 5 ml of concentrated sulfuric acid and 0.8 ml (0.5 equivalents) of 2,4-pentanedione. The resulting mixture was stirred at 25° C. for a period of about 100 minutes. An aliquot sample of the reaction mixture was analyzed by thin-layer chromatography (elution with 30% ethylacetate in hexanes) which showed that 2-acetylbenzo[b]thiophene was forming as a reaction product.

EXAMPLE 8

Preparation of 2,2'-Dithiobis(benzaldehyde) by Oxidation of 2,6-Dithio-9-oxa-dibenzo[c,g]bicyclo-[3.3.1]nonane 2,6-Dithio-9-oxa-dibenzo[c,g]bicyclo-[3.3.1]nonane (0.10 g, 0.387 mmol) and 5 ml of concentrated sulfuric acid were placed in a 25 ml round-bottom flask and the resulting mixture was stirred at ambient temperature for about 100 minutes. An aliquot sample of the reaction mixture was analyzed by thin-layer chromatography, eluting with 30% ethyl acetate in hexanes. Analysis of the reaction mixture by $^1$H NMR showed that the predominant reaction product was 2,2'-dithiobis(benzaldehyde).

The foregoing examples are provided to enable one skilled in the art to practice the process of the present invention and are not to be viewed as limiting the scope of the invention as it is defined by the appended claims.

We claim:

1. A process for the preparing a 2-acetylbenzo[β]thiophene of the structure

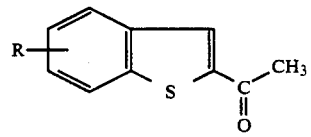

wherein R is selected from hydrogen, alkyl of from one to six carbon atoms, and alkoxy of from one to six carbon atoms, comprising the steps of a) reacting a derivative of benzaldehyde having the structure

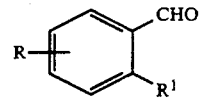

wherein R is as defined above and $R^1$ is chlorine or bromine with a sterically encumbered mercaptan of from three to twelve carbon atoms in the presence of a base to form a 2-alkylthiobenzaldehyde of the formula

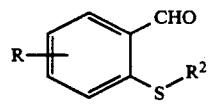

where R is as defined above and $R^2$ is alkyl of from three to twelve carbon atoms;

b) reacting the product of step a) with an oxidizing agent in the presence of an acid to produce a 2,2'-dithiobis(benzaldehyde) of the formula

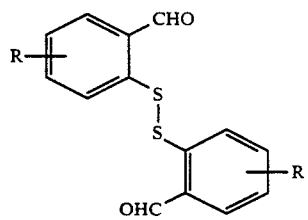

wherein R is as defined above; and c) reacting the product of step b) with a compound of the structure R³CH₂C(O)CH₃ to produce a 2-acetylbenzo[β]thiophene of the structure

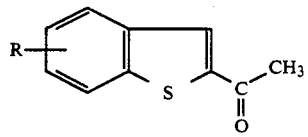

wherein R is as defined above and R³ is halogen or CH₃C(O)—.

2. The process as defined by claim 1 wherein R is hydrogen.

3. The process as defined by claim 2 wherein said derivative of benzaldehyde is 2-chlorobenzaldehyde.

4. The process as defined by claim 1 wherein said sterically encumbered mercaptan is 1,1-dimethylethanethiol.

5. The process as defined by claim 1 wherein said oxidizing agent is selected from the group consisting of bromine; chlorine; cupric acetate; cupric chloride; HOCl; HOBr; N-bromo-succinimide; N-chlorosuccinimide; sodium bromate; potassium bromate, sodium iodate; and potassium iodate.

6. The process as defined by claim 5 wherein said oxidizing agent is bromine.

7. The process as defined by claim 1 wherein step b) is carried out in the presence of hydrogen bromide in a reaction mixture comprising dimethylsulfoxide.

8. The process as defined in claim 1 wherein step c) is carried out by sequentially c1) first reacting the 2,2'-dithiobis(benzaldehyde) product of step b) with about one equivalent of 2,4-pentanedione in the presence of base, and c2) subsequently reacting the product of step c1) with about one equivaent of a haloacetone and thereafter separating the product 2-acetylbenzo[b]thiophene from the reaction mixture 9. The process as defined by claim 8 wherein said haloacetone is chloroacetone.

10. The process as defined by claim 1 comprising the step of converting the product of step a) to a 2,6-dithio-9-oxa-dibenzo[c,g]bicyclo[3.3.1]nonane intermediate and subsequently converting said intermediate to a 2,2'-dithiobis(benzaldehyde).

11. A process for preparing a 2-acetylbenzo[β]thiophene of the structure

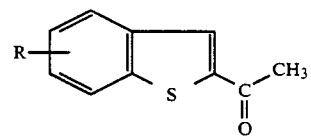

wherein R is selected from hydrogen, alkyl of from one to six carbon atoms, and alkoxy of from one to six carbon atoms, comprising the steps of a) reacting a 2-alkylthiobenzaldehyde of the formula

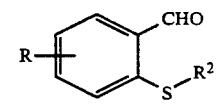

wherein R is selected from hydrogen, alkyl of from one to six carbon atoms, and alkoxy of from one to six carbon atoms with chlorine to produce a compound of the structure

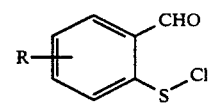

where R is as defined above; and b) reacting the product of step a) with a compound of the structure R³CH₂C(O)CH₃ where R³ is selected from CH₃C(O) and Cl to produce a 2-acetylbenzo[β]thiophene of the structure

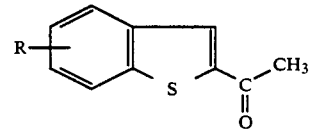

wherein R is as defined above.

12. The process as defined by claim 11 wherein step b) is carried out by sequentially b1) first reacting one equivalent of the product of step a) with about one equivalent of 2,4-pentanedione in the presence of base, and b2) subsequently adding about one equivalent of a haloacetone to the reaction mixture.

13. The process as defined by claim 12 wherein said haloacetone is chloroacetone.

14. A process for the preparation of 2-acetylbenzo[b]thiophene comprising the steps of a) reacting 2-chlorobenzaldehyde with 1,1-dimethylethanethiol in the presence of a base to form 2-(1,1-dimethylethylthio)benzaldehyde;

b) reacting the product of step a) with bromine in the presence of acid to produce 2,2'-dithiobis(benzaldehyde); and c) reacting the product of step b) sequentially with about one equivalent of acetoacetone in the presence of base and then subsequently with one equivalent of chloroacetone in the presence of base to produce 2-acetylbenzo[β]thiophene.

* * * * *